United States Patent
Ma et al.

(10) Patent No.: US 6,696,053 B1
(45) Date of Patent: Feb. 24, 2004

(54) LEAVE-ON OR RINSE-OUT HAIR CARE CONDITIONER COMPOSITIONS CONTAINING SILICONE QUATERNARY COMPOUNDS AND THICKENERS

(75) Inventors: Zhuning Ma, Schaumburg, IL (US); John Edward Wydila, Schaumburg, IL (US); Mark Dailey, II, Chicago, IL (US); Loralei Marie Brandt, Cary, IL (US); Paul Howard Neill, Hinsdale, IL (US)

(73) Assignee: Unilever Home & Personal Care USA, division of Conopco, Inc., Chicago, IL (US)

( * ) Notice: Subject to any disclaimer, the term of this patent is extended or adjusted under 35 U.S.C. 154(b) by 0 days.

(21) Appl. No.: 09/564,932

(22) Filed: May 4, 2000

(51) Int. Cl.$^7$ .......................... A61K 7/075; A61K 7/08; A61K 7/06; A61K 7/11
(52) U.S. Cl. ................ 424/70.27; 424/70.1; 424/70.11; 424/70.12; 424/70.28
(58) Field of Search .............................. 424/70.1, 70.11, 424/70.12, 70.27, 70.28

(56) References Cited

U.S. PATENT DOCUMENTS

| | | | |
|---|---|---|---|
| 3,964,500 A | | 6/1976 | Drakoff |
| 4,152,416 A | | 5/1979 | Spitzer et al. |
| 4,364,837 A | | 12/1982 | Pader |
| 4,749,565 A | * | 6/1988 | Grollier |
| 5,034,218 A | | 7/1991 | Duvel |
| 5,665,337 A | | 9/1997 | Carballada et al. |
| 5,679,114 A | | 10/1997 | Haning et al. |
| 5,976,557 A | | 11/1999 | Friedrich et al. |
| 6,028,041 A | | 2/2000 | Decoster et al. |
| 6,143,286 A | * | 11/2000 | Bhambhani et al. |

FOREIGN PATENT DOCUMENTS

WO          04/01076          1/1994

OTHER PUBLICATIONS

International Search Report Application No. PCT/EP 01/04878 mailed Dec. 3, 2001.

* cited by examiner

*Primary Examiner*—Thurman K. Page
*Assistant Examiner*—Humera N. Sheikh

(57) ABSTRACT

The present invention relates to a leave-on or rinse-out hair conditioning or styling aid composition that comprises:
  a) a silicone quaternary compound,
  b) a cationic thickener, and
  c) a carrier, wherein said carrier is water, or a hydroalcoholic solvent; and wherein said composition is substantially lacking in fatty alcohol.

20 Claims, No Drawings

LEAVE-ON OR RINSE-OUT HAIR CARE CONDITIONER COMPOSITIONS CONTAINING SILICONE QUATERNARY COMPOUNDS AND THICKENERS

BACKGROUND OF THE INVENTION

Most individuals buy and use a hair shampoo for its cleansing properties. In addition to having clean hair, a consumer also desires sufficiently conditioned hair that holds a preset configuration. However, hair shampoos are generally formulated with highly effective anionic surfactants that primarily clean as opposed to condition the hair. Anionic surfactants not only remove the dirt and soil from hair, but also remove sebum naturally present on the surface of hair fibers. Therefore, the desirable cleansing properties of anionic surfactants also can leave hair in a cosmetically unsatisfactory condition. Shampoos also do not detangle wet hair and do not impart residual conditioning benefits to dry hair such as manageability or styleability of hair sets.

In general, shampoo compositions containing anionic surfactants, or nonionic surfactants or amphoteric surfactants, leave hair with an undesirable harsh, dull and dry touch, or feel, after the hair is shampooed and then rinsed with water. Furthermore, thoroughly cleansed hair also is extremely difficult to comb, in either the wet or the dry state, because the individual hair fibers tend to snarl, kink, and interlock with each other. In addition, incompletely dried hair, such as hair dried with a towel, has poor brushing properties, and after complete drying, the hair does not set well. The combing or brushing properties of dry hair remain poor, and the hair has undesirable electrostatic properties in a low humidity atmosphere that causes the hair to "fly away" thereby further reducing the brushing properties of the hair.

The unsatisfactory combing or brushing properties of hair immediately after shampooing or during trimming treatments after shampooing also causes hair damage such as split ends or hair breakage. In addition the natural luster and resiliency of hair is reduced. The overall unsatisfactory condition of shampooed hair often makes necessary a subsequent post shampoo treatment of the hair with a conditioning composition to improve these undesirable physical characteristics. Conditioning compositions typically are applied separately from the hair shampoo, and usually are rinses, cream-like emulsions or lotions containing a cationic compound.

Therefore, the consumer has traditionally shampooed the hair to cleanse the hair, and followed this with the application of a conditioner composition to improve wet combing. The commonly accepted method has been to shampoo the hair, followed by rinsing the hair, and then applying a conditioner composition, followed by a second rinse. The wet combing problem has been solved by treating shampooed hair with a conditioner composition that coats the hair shaft and causes individual hair fibers in to resist tangling and matting because of the conditioner residue retained on the hair shaft.

Conventional leave-on or rinse-out hair conditioners rely on fatty alcohols to build viscosity, and on alkyl quaternaries and silicones to provide conditioning. While these conventional leave-on or rinse-out hair conditioners, do condition the hair, the fatty alcohols tend to deposit on the hair surface along with the conditioning agents, thereby weighing down the hair. Therefore, hair that has been conditioned with these conventional leave-on or rinse-out hair conditioners tends to have less body than unconditioned hair.

It would be desirable to develop a leave-on or rinse-out hair conditioner composition that does not thereby substantially decrease natural hair body. It would also be desirable for a leave-on or rinse-out hair conditioner to incorporate a water-soluble styling resin, to deliver a hair styling benefit. It would also be desirable to provide such a leave-on or rinse-out styling conditioner at low cost. Compositions of the present invention have these properties.

Publications related to the invention are as follows:

U.S. Pat. No. 5,679,114 discloses hair treatment compositions for temporarily coloring the hair which contain a polymer and a metal containing pigment.

U.S. Pat. No. 5,034,218 discloses stable conditioning shampoos containing a compatible anionic surfactant/cationic conditioning agent, non-volatile silicone emulsion.

U.S. Pat. No. 5,665,337 discloses compositions which comprise from about 0.25% to about 70% of a copolymer component comprising from about 1.5% to about 70% of a silicone-grafted adhesive hair styling copolymer having a weight average molecular weight from about 300,000 to about 5.000,000 and from about 30% to about 98.5% of a hydrophobic volatile solvent.

U.S. Pat. No. 4,749,565 discloses cosmetic compositions based on cationic silicone, water-soluble heteropolysaccharide and electrolyte.

SUMMARY OF THE INVENTION

The present invention relates to a leave-on or rinse-out hair conditioning composition, which comprises:

a) a silicone quaternary compound;

b) a cationic thickener; and c) a carrier, wherein said carrier is selected from the group consisting of water, a hydroalcoholic solvent and a mixture thereof;

and wherein said composition is substantially lacking in fatty alcohol.

The present invention also relates to a method for conditioning and styling hair which comprises contacting said hair with an effective amount of a composition of the invention.

DETAILED DESCRIPTION OF THE INVENTION

As used herein % means weight % of the total composition, unless otherwise indicated. "Fatty alcohol" means an alcohol of 8 carbons or more. "Substantially lacking in fatty alcohol" means a level of fatty alcohol in the composition that is so low that upon use on the hair, said fatty alcohol does not cause the hair to lose its natural body. Usually the level of fatty alcohols in the compositions of the invention is less than about 0.2% fatty alcohol. More preferably, compositions of the invention has than 0.1% fatty alcohol or less than 0.05% fatty alcohol. The term "leave-on" refers to a hair care composition that is applied to the hair and not further subjected to a rinsing step. The term "rinse-out" as contrasted with the term "leave-on" is used herein to mean compositions which are used in a context whereby the composition is ultimately rinsed or washed from the hair either after or during the application of the product.

Leave-on or rinse-out compositions of the invention may take the form of providing the hair with styling benefits, and in particular allowing the hair to retain a given style for a longer period of time. In this context the word "style" is given its usual meaning in the art, which is the act of creating a style in the hair, often after some initial drying. In any event the act of styling usually requires that the hair retain a given configuration, with individual hair shafts generally retaining their configuration relative to each other.

The benefits from compositions of the invention may be derived whether the hair is dried with a hair dryer, or allowed to dry naturally.

Traditional hair conditioning compositions rely upon fatty alcohols to build viscosity. However, fatty alcohols tend to deposit on the hair surface along with the conditioning agents resulting in less body than unconditioned hair. The compositions of the invention are substantially lacking in fatty alcohol and thereby avoid this problem. After treatment with compositions of the invention, hair is left with more of its natural body.

The starting materials used in preparing the compositions of the invention are either known or can be prepared according to known methods. Compositions of the invention can be prepared by known methods, or by methods that are analogous to known methods.

The present invention relates to a leave-on or rinse-out hair conditioning composition that comprises:

a) a silicone quaternary compound, b) a cationic thickener; and c) a carrier, wherein said carrier is selected from the group consisting of water, a hydroalcoholic solvent and a mixture thereof;

and wherein said composition is substantially lacking in fatty alcohol.

The compositions of the invention are oil-in-water dispersions and/or emulsions. In compositions of the invention, there is a combination of a silicone quaternary compound and a cationic thickener.

The ingredients employed in the compositions of the invention are as follows:

Silicone Quaternary Compounds

Silicone quaternary ammonium compounds that may be employed in the compositions of the invention include cationic silicone derivatives, such as Quaternium-80, having the structure set forth on volume 1, pages 631 and 632 of the International Cosmetic Ingredient Dictionary, fifth edition, 1993, editor Wenninger et al, which is hereby incorporated by reference.

Cationic Thickener

Compositions of the invention also comprise a cationic thickener. Non-limiting examples of cationic thickeners that can be used in compositions of the invention include cationic acrylates, most preferably Salcare SC 96. Salcare SC 96 is available from Ciba Specialty Chemicals, as a liquid dispersion polymer composition.

The composition of Salcare SC 96 is approximately 44% by weight Polyquaternium-37 polymer. Polyquaternium-37 polymer is a water swellable polymer and is also referred to as N,N,N-trimethyl-2((methyl-1-oxo-2-propenyl)oxy), chloride polymer and which has the chemical structure set forth at page 1145 having the structure set forth on volume 2, page 1145 of the International Cosmetic Ingredient Dictionary, eighth edition, 2000, editor Wenninger et al, which is hereby incorporated by reference.

The remainder of the Salcare SC 96 polymer composition is described as comprising a mixture of propylene glycol/dicaprylate/dicaprate 50% propyleneglycol-1 trideceth 6 at 6%.

Other cationic thickeners which may be used include Salcare 95 which is dimethylaminoethylmethacrylate homopolymer; SC 10 which is dimethylammonium chloride acrylamide; and SC 60 which is copolymer of acrylamidylpropyltriammonium chloride.

Carrier

Compositions of the invention also comprise water, preferably, deionized water. The compositions of the invention may also comprise hydroalcoholic solvent.

Optional Ingredients

Non-volatile Silicone Compounds

Other non-volatile silicone quaternary compounds that may be used are silicone compounds that are included in the oil phase of compositions of the invention. The preferred other silicone compounds are polyalkylsiloxanes such as polydimethylsiloxane, and polymethylphenylsiloxane. Polydimethylsiloxanes, which are also known as dimethicones, are especially preferred. The polyalkylsiloxanes that can be used include, for example, polydimethylsiloxanes. These silicone compounds are available, for example, from the General Electric Company in their Viscasil R and SF 96 series, and from Dow Corning in their Dow Corning 200 series.

Polyalkylaryl siloxane fluids can also be used and include, for example, polymethylphenylsiloxanes. These siloxanes are available, for example, from the General Electric Company as SF 1075 methyl phenyl fluid or from Dow Corning as 556 Cosmetic Grade Fluid.

The silicone compounds that can be used also include, for example, a polypropylene oxide modified polydimethylsiloxane, although ethylene oxide or mixtures of ethylene oxide and propylene oxide modified polydimethylsiloxanes can also be used. The ethylene oxide and polypropylene oxide level should be sufficiently low so as not to interfere with the dispersibility characteristics of the silicone. These materials are also known as dimethicone copolyols.

Other silicone compounds include amino substituted materials such as suitable alkylamino substituted silicone compounds. An especially preferred amino substituted silicone is the polymer known as trimethylsilylamodimethicone. A preferred polymer of this class is available from Union Carbide under the name "UCAR SILICONE ALE 56." References disclosing suitable nonvolatile dispersed silicone compounds include U.S. Pat. No. 2,826,551, to Geen; U.S. Pat. No. 3,964,500, to Drakoff, issued Jun. 22, 1976; U.S. Pat. No. 4,364,837, to Pader; and British Patent No. 849,433, to Woolston.

Another nonvolatile dispersed silicone that can be especially useful is a silicone gum. The term "silicone gum", as used herein, means a polyorganosiloxane material having a viscosity at 250 degrees C of greater than or equal to 1,000,000 centistokes. It is recognized that the silicone gums described herein can also have some overlap with the above-disclosed silicone compounds. This overlap is not intended as a limitation on any of these materials. Silicone gums are described in U.S. Pat. No. 4,152,416, to Spitzer et al., issued May 1, 1979 and Noll, Walter, Chemistry and Technology of Silicones, New York: Academic Press 1968. Also describing silicone gums are General Electric Silicone Rubber Product Data Sheets SE 30, SE 33, SE 54 and SE 76. The "silicone gums" will typically have a mass molecular weight in excess of about 200,000, generally between about 200,000 and about 1,000,000. Specific examples include polydimethylsiloxane, poly(dimethylsiloxane methylvinylsiloxane) copolymer, poly (dimethylsiloxane diphenylsiloxane methylvinylsiloxane) copolymer and mixtures thereof.

Also useful are silicone resins, which are highly crosslinked polymeric siloxane systems. The crosslinking is introduced through the incorporation of tri-functional and tetra-functional silanes with mono-functional silanes or di-functional silanes, or both types of silanes during manufacture of the silicone resin. As is well understood in the art, the degree of crosslinking that is required in order to result in a silicone resin will vary according to the specific silane units incorporated into the silicone resin. In general, silicone materials which have a sufficient level of trifunctional and tetrafunctional siloxane monomer units, and hence, a sufficient level of crosslinking, such that they dry down to a rigid, or hard, film are considered to be silicone resins. The ratio of oxygen atoms to silicon atoms is indicative of the level of crosslinking in a particular silicone material. Silicone materials that have at least about 1.0 oxygen atoms per silicon atom will generally be silicone resins herein. Preferably, the ratio of oxygen to silicon atoms is at least about 1.2 to 1.0. Silanes used in the manufacture of silicone resins include monomethyl-, dimethyl-, trimethyl-, monophenyl-, diphenyl-, methylphenyl-, and monovinyl-, with the methyl substituted silanes being most commonly utilized. General Electric as GE SS4230 and SS4267 offers preferred resins. Commercially available silicone resins will generally be supplied in a dissolved form in a low viscosity volatile or nonvolatile silicone fluid. The silicone resins for use herein can be supplied and incorporated into the present compositions in such dissolved form, as will be readily apparent to those skilled in the art.

Other useful silicone resins are silicone resin powders such as the material given the CTFA designation polymethylsilsequioxane, which is commercially available as "Tospearl" from Toshiba Silicones.

The method of manufacturing these silicone compounds, can be found in Encyclopedia of Polymer Science and Engineering, Volume 15, Second Edition, pp. 204–308, John Wiley & Sons, Inc., 1989.

Commercially available silicone compounds which are useful herein include Dimethicone with tradename D-130, cetyl Dimethicone with tradename DC2502, stearyl Dimethicone with tradename DC2503, emulsified polydimethyl siloxanes with tradenames DC1664 and DC1784, and alkyl grafted copolymer silicone emulsion with tradename DC2-2845; all available from Dow Corning Corporation, and emulsion polymerized Dimethiconol available from Toshiba Silicone as described in GB application 2,303,857.

Amino Silicones

An especially preferred cationic silicone derivative is that sold under the tradename "Dow Corning 929 (DC 929)" cationic emulsion by DOW CHEMICAL COMPANY, which contains in combination (1) "amodimethicone,"

(2) "tallowtrimonium chloride," and (3) "nonoxynol-10."

Mixtures of the silicone quaternary compounds described above can also be used in the compositions of the invention.

Volatile Silicones

The silicone oil phase of the compositions of the invention can also comprise a volatile silicone oil. By "volatile" is meant that the oil has a boiling point less than about 225 degrees Celsius at 760 mm Hg. Exemplary volatile silicone compounds include, but are not limited to, volatile, low molecular weight polydimethylsiloxane compounds. They can be either a linear or a cyclic polydimethylsiloxane compound having a viscosity from about 0.5 to about 10 cst (centistokes). The preferred linear polydimethylsiloxane compounds can have a viscosity range from about 0.5 to 10cst. The preferred volatile polydimethylsiloxanes have a viscosity in the range of about 0.5 to about 6 cst.

The cyclic, volatile, low molecular weight polydimethylsiloxanes, designated in the CTFA Dictionary as cyclomethicones, optionally used in compositions of the present invention. The cyclic volatile siloxanes can be D4, D5, or D6, and mixtures thereof); boil at atmospheric pressure at from about 35° C. to about 250° C. The polydimethyl cyclosiloxanes having an average of about 4 to about 5 repeating units per molecule are especially preferred. Suitable cyclomethicones are available commercially under the trade names DOW CORNING 244 Fluid, DOW CORNING 245 Fluid, DOW CORNING 344 Fluid and DOW CORNING 345 Fluid from DOW CORNING Corporation, Midland, Mich., and SILICONE SF-1173 and SILICONE SF-1202 from General Electric, Waterford, N.Y.

An example of a linear, low molecular weight, volatile polydimethylsiloxane compound is designated in the CTFA Dictionary as decamethyltetrasiloxane, available commercially under the trade name DOW CORNING 200 Fluid having a viscosity of 0.5 to 1.5 cst. Other linear polydimethylsiloxanes include octamethyltrisiloxane, decamethylpentasiloxane and mixtures thereof which also be useful in the compositions of the invention.

Other volatile silicones useful in compositions of the invention include phenyl pentamethyldisiloxane, phenyl pentaethyldisiloxane, methoxy propylheptamethyldisiloxane, and mixtures thereof. Mixtures of the silicones described above can also be used in the compositions of the invention.

Styling Resins

When it is desired to produce a composition of the invention that also has styling properties, a water-soluble styling resin can be included in such compositions.

Water-soluble styling resins include Copolymer 845, Gafquat 755N, Gafquat H5100, Styleze CC-10 (a quaternized polyacrylate), Celquat L200 and Chitosan PCA.

Waxes

When it is desired to opacify the compositions of the invention, so that they look like traditional hair conditioners, waxes can be added to said compositions. Such waxes may be selected from the group consisting of paraffin wax, beeswax, microcrystalline wax, ozokerite wax, carnauba wax, and candelilla wax, and mixtures thereof. Mixed hydrocarbon silicone waxes may also be used. Most preferred is paraffin wax. Paraffin waxes can include Paraffin Wax 206 which melts at 50 to 53 degrees Celsius, Paraffin Wax 1275 which melts at 53 to 58 degrees Celsius, and Paraffin Wax 674 which melts at 69 to 73 degrees Celsius. As noted above such waxes opacify compositions of the invention. However, such waxes do not affect hair body attributes, as do fatty alcohols that have been traditionally used in hair conditioning compositions.

Other Ingredients

Compositions of the invention can optionally include pearlescent aids such as ethylene glycol distearate; preservatives such as benzyl alcohol, methyl paraben, propyl paraben, and imidazolidinyl urea; pH adjusting agents such as citric acid, sodium citrate, succinic acid, phosphoric acid, sodium hydroxide, and sodium carbonate; coloring agents such as FD&C or D&C dyes; and perfumes.

Ranges of Ingredients Which may be Used in Compositions of the Invention

Ingredients in the compositions of the invention may fall within the following ranges:

a) silicone quaternary compound, from about 0.1 to about 6% b) cationic thickener, from about 0.25 to about 5% c) optional volatile silicone, from about 0.2 to about 6% d) optionally water soluble styling resin, about 0.2 to about 8% e) optional other silicone from about 0.2 to about 6%.

f) optional wax from about 0.1 to about 6% g) carrier, qs

Ingredients in the compositions of the invention more preferably fall within the following ranges:

a) silicone quaternary compound, from about 0.2 to about 2% b) cationic thickener from about 0.5 to about 2.5% c) optional volatile silicone from about 0.2 to about 6% d) optionally water soluble styling resin from about 0.2 to about 8% e) optional other silicone from about 0.2 to about 6% f) optional wax from about 0.1 to about 6% g) carrier, q.s.

Method of Using Compositions of the Invention

The invention also relates to a method for styling and/or conditioning hair (without decreasing natural hair body) which comprises contacting said hair with an effective amount of a composition of the invention.

Typically, a rinse-out composition of the invention is worked into wet hair (immediately after a shampoo and rinse) usually with the fingers; the composition may then be rinsed off, then the hair is combed or brushed. The hair is then dried with a towel or a blow dryer. Alternatively, a composition of the invention may be applied to dry hair simultaneously with the application of water. Alternatively, compositions of the invention may be applied to dry hair and then afterwards additional water may be applied to the hair in a rinsing step. These rinse-out compositions of the invention supply a conditioning benefit to the hair.

Compositions of the invention can also be leave-on conditioners. Such compositions are typically applied with the fingers to wet hairs, or to dry hair; or to dry hair that is subsequently wetted followed by working the hair with a comb or a brush. The composition is then left in the hair and the hair may dried with a towel or a blow dryer. These leave-on compositions of the invention supply a conditioning benefit to the hair. Where these leave-on compositions of the invention may also contain a styling agent, said compositions will also supply a styling benefit to the hair.

The following specific compositions of the invention were made. The examples that follow are intended to illustrate the invention without in any way being limited in nature.

| INGREDIENTS | WEIGHT PERCENT OF INGREDIENTS | | |
| --- | --- | --- | --- |
| | EXAMPLE 1 | EXAMPLE 2 | EXAMPLE 3 |
| QUATERNIUM 80 | 0.33 | 1.0 | 0.63 |
| DC 245 FLUID | 0.33 | 1.0 | 4.38 |
| SALCARE SC 96 | 0.33 | 1.0 | 2.0 |
| FRAGRANCE | 0 | 0 | 0.5 |
| WATER | 99.01 | 97 | 92.49 |
| TOTAL | 100 | 100 | 100 |

| | EXAMPLE 4 | EXAMPLE 5 |
| --- | --- | --- |
| Water | 93.53 | 86.78 |
| Quaternium-80 | 0.3 | 0.3 |
| Paraffin Wax 206 | 0.85 | 0.81 |
| Beeswax | 0 | 0.04 |
| Salcare SC 96 | 1.67 | 1.67 |
| DC245 Fluid | 2.5 | 2.5 |
| Preservative | 0.2 | 0.2 |

-continued

| INGREDIENTS | WEIGHT PERCENT OF INGREDIENTS | |
| --- | --- | --- |
| Fragrance | 0.2 | 0.2 |
| PVP/VA | 0.75 | 7.5 |
| TOTAL | 100 | 100 |

The compositions of examples 4 and 5 were made as follows:

1.) A premix of pvp/va and deionized water was made.

2.) The water was heated to 82° Celsius.

3.) The wax was melted fully. Quaternium-80 was added.

4.) The mixing speed was increased to 1800 rpm.

5.) The mixture was checked for particles. The batch was cooled slowly.

6.) The premix blend was added at 38° Celsius.

7.) Other ingredients were added at about 32° Celsius.

| INGREDIENTS | WEIGHT PERCENT OF INGREDIENTS | |
| --- | --- | --- |
| | EXAMPLE 6 | EXAMPLE 7 |
| Quaternium-80 | 0.5 | 0.495 |
| DC 245 fluid | 4.0 | 2.48 |
| Salcare SC 96 50% | 3.3 | 2.35 |
| Fragrance | 0.5 | 0.4 |
| Paraffin Wax | 1.7 | 1.0 |
| Preservative | 0.3 | 0.3 |
| Water | 89.7 | 91.975 |
| Dow DC 929, 35% | 0 | 1.0 |
| TOTAL | 100 | 100 |
| | EXAMPLE 8 | EXAMPLE 9 |
| Quaternium-80 | 0.5 | 0.5 |
| DC 245 fluid | 2.0 | 4.0 |
| Salcare SC 96 50% | 1.15 | 1.3 |
| Fragrance | 0.125 | 0.05 |
| Preservative | 0.2 | 0.2 |
| Water | 96.025 | 93.95 |
| TOTAL | 100 | 100 |

Benefits of Compositions of the Invention

Wet combing studies have shown that compositions of the invention impart good wet combing properties and conditioning properties to the hair.

Trained sensory panels could be used to show that repeated daily use of rinse-out compositions of the invention leave hair with more body and styleability than conditioners containing fatty alcohols.

Trained sensory could be used to show that repeated daily use of leave-on compositions of the invention leave hair with more body and style than conditioners containing fatty alcohols.

What is claimed is:

1. A leave-on or rinse-out hair conditioning or styling composition which comprises:

a) from about 0.1 to about 6% of a cationic silicone quaternary compound;

b) from about 0.25 to about 5% of a cationic thickener;

c) from about 0.2 to about 6% of a volatile silicone; and d) a carrier, wherein said carrier is selected from the group consisting of water, a hydroalcoholic solvent and a mixture thereof;

and wherein said composition has less than 0.05% fatty alcohol.

2. A composition according to claim 1, which comprises
   a) from about 0.2% to about 2% of a cationic silicone quaternary compound;
   b) from about 0.5% to about 2.5% of a cationic thickener; and
   c) a carrier.

3. A composition according to claim 1, wherein said cationic silicone quaternary compound is Quaternium-80.

4. A composition according to claim 1, wherein said Quaternium-80 is present at from about 0.1 to about 6%.

5. A composition according to claim 4, wherein said Quaternium-80 is present at from about 0.2 to about 2%.

6. A composition according to claim 1, wherein the cationic thickener is dimethylammonium chloride acrylamide.

7. A composition according to claim 1, wherein the cationic thickener is copolymer of acrylamidylpropyltriammonium chloride.

8. A composition according to claim 1, wherein the cationic thickener is N,N,N-trimethyl-2((methyl-1-oxo-2-propenyl)oxy), chloride polymer.

9. A composition according to claim 1, which is a leave-on or rinse-out hair conditioner.

10. A composition according to claim 1, which is a leave-on or rinse-out styling hair conditioner.

11. A composition according to claim 1, which further comprises from about 0.2% to about 8% of a styling resin.

12. A composition according to claim 1, which further comprises from about 0.2% to about 4% of a styling resin.

13. A composition according to claim 1, which further comprises from about 0.2% to about 3% of a styling resin.

14. A composition according to claim 10, which further comprises a styling resin which is polyvinyl pyrrolidone/vinyl acetate.

15. A composition according to claim 1, which further comprises from about 0.1% to about 8% of a wax.

16. A composition according to claim 1, which further comprises from about 0.25% to about 4% of a wax.

17. A composition according to claim 1, which further comprises from about 0.25% to about 2% of a wax.

18. A method for conditioning hair that comprises contacting said hair with an effective amount of a composition according to claim 1.

19. A leave-on or rinse-out hair conditioning or styling composition which comprises:
   a) from about 0.1 to about 6% of a cationic silicone quaternary compound;
   b) from about 0.25 to about 5% of a cationic thickener;
   c) from about 0.2 to about 8% of a water soluble styling resin; and
   d) a carrier, wherein said carrier is selected from the group consisting of water, a hydroalcoholic solvent and a mixture thereof;

and wherein said composition has less than 0.05% fatty alcohol.

20. A composition according to claim 19 wherein the styling resin is a polymer formed of a monomer selected from the group consisting of vinyl pyrrolidone, vinyl acetate, acrylate and mixtures thereof.

* * * * *